(12) United States Patent
Salomir et al.

(10) Patent No.: US 9,375,588 B2
(45) Date of Patent: Jun. 28, 2016

(54) METHOD AND SYSTEM FOR GUIDED SHIELDING OF A PATIENT VOLUME FROM ULTRASOUND ENERGY

(75) Inventors: Rares Salomir, Ambilly (FR); Magalie Viallon, Lyons (FR); Lorena Petrusca, Annemasse (FR); Vincent Auboiroux, Annemasse (FR); Thomas Goget, Annemasse (FR); Maria Isabel Vargas Gomez, Genéve (CH)

(73) Assignee: Siemens Aktiengesellschaft, München (DE)

( * ) Notice: Subject to any disclaimer, the term of this patent is extended or adjusted under 35 U.S.C. 154(b) by 615 days.

(21) Appl. No.: 13/303,872

(22) Filed: Nov. 23, 2011

(65) Prior Publication Data

US 2013/0131494 A1  May 23, 2013

(51) Int. Cl.
*A61B 5/05* (2006.01)
*A61N 7/02* (2006.01)
*A61B 19/00* (2006.01)

(52) U.S. Cl.
CPC .............. *A61N 7/02* (2013.01); *A61B 19/5225* (2013.01); *A61B 2019/4036* (2013.01); *A61B 2019/4045* (2013.01); *A61B 2019/4054* (2013.01); *A61B 2019/5236* (2013.01); *A61B 2019/5265* (2013.01)

(58) Field of Classification Search
CPC ........ A61B 6/107; A61B 6/4405; G21F 3/00; A61N 5/1048; G10K 11/002
USPC .............................. 600/1, 427, 411; 389/98.4
See application file for complete search history.

(56) References Cited

U.S. PATENT DOCUMENTS

| | | | | |
|---|---|---|---|---|
| 4,655,205 A | * | 4/1987 | Hepp et al. ..................... | 128/846 |
| 5,073,253 A | * | 12/1991 | Bishop .......................... | 209/164 |
| 5,602,895 A | * | 2/1997 | Fivez et al. ................... | 378/98.4 |
| 2001/0027260 A1 | * | 10/2001 | Uematsu et al. .................. | 600/1 |
| 2002/0115990 A1 | * | 8/2002 | Acker ............................ | 606/27 |
| 2009/0232282 A1 | * | 9/2009 | Belson et al. ................. | 378/203 |

OTHER PUBLICATIONS

Ballard, J. R., et al., "Adaptive Transthoracic Refocusing of Dual-Mode Ultrasound Arrays," IEEE Trans Biomed Eng., vol. 57, No. 1, Jan. 2010, pp. 93-102.
Civale, J., et al., "The Use of a Segmented Transducer for Rib Sparing in HIFU Treatments,"Ultrasound in Med. & Biol., vol. 32, No. 11, 2006, pp. 1753-1761.

(Continued)

*Primary Examiner* — Long V Le
*Assistant Examiner* — Helene Bor
(74) *Attorney, Agent, or Firm* — Lempia Summerfield Katz LLC

(57) ABSTRACT

In order to decrease collateral heating of ribs and tissue surrounding the ribs in a patient during high-intensity focused ultrasound (HIFU) therapy, shielding material may be positioned on or adjacent to an external surface of the patient and aligned with ribs to be protected using a magnetic resonance imaging (MRI) system. The MRI system may be used to image the shielding material and the ribs to be protected, and an error of alignment between the ribs to be protected and the shielding material may be determined based on the images. The shielding or masking material may be repositioned based on the determined error of alignment, images of the shielding material and the ribs to be protected may be reacquired, and the error of alignment may be redetermined based on the reacquired images until the shielding material is aligned with the ribs to be protected.

24 Claims, 6 Drawing Sheets

(56) References Cited

OTHER PUBLICATIONS

Quesson, B., et al., "A method for MRI guidance of intercostal high intensity focused ultrasound ablation in the liver," Medical Physics, vol. 37, No. 6, Jun. 2010, pp. 2533-2540.

Tanter, M., et al., "Compensating for bone interfaces and respiratory motion in high-intensity focused ultrasound," Int. J. Hyperthermia, vol. 23, No. 2, 2007, pp. 141-151.

Zhu, H., et al., "High intensity focused ultrasound (HIFU) therapy for local treatment of hepatocellular carcinoma: Role of partial rib resection," European Journal of Radiology, vol. 72, 2009, pp. 160-166.

Tomlinson, J. S., et al., "Actual 10-Year Survival After Resection of Colorectal Liver Metastases Defines Cure," Journal of Clinical Oncology, vol. 25, No. 29, 2007, pp. 4575-4580.

Yan, B. C., et al., "Recent Developments in Liver Pathology," Arch Pathol Lab Med., vol. 133, 2009, pp. 1078-1086.

Botros, Y. Y., et al., "A Hybrid Computational Model for Ultrasound Phased-Array Heating in Presence of Strongly Scattering Obstacles," IEEE Transactions on Biomedical Engineering, vol. 44, No. 11, 1997, pp. 1039-1050.

Mayo, S. C., et al., "Current management of colorectal hepatic metastasis," Expert Rev. Gastroenterol Hepatol, vol. 3, No. 2, 2009, pp. 131-144.

\* cited by examiner

METHOD AND SYSTEM FOR GUIDED SHIELDING OF A PATIENT VOLUME FROM ULTRASOUND ENERGY

FIELD

The present embodiments relate to a method for positioning shielding material used to prevent ultrasound energy from reaching a volume to be protected.

BACKGROUND

High-intensity focused ultrasound (HIFU) therapy is a minimally invasive or non-invasive method used to deposit acoustic energy into tissue such as a tumor on the liver of a patient. In HIFU therapy, an HIFU beam is used to heat and destroy the tumor through ablation. During HIFU therapy of the liver, there is a high risk of collateral heating and thermal damage to healthy tissue adjacent to the liver such as, for example, ribs and tissue surrounding the ribs.

A linearly segmented HIFU transducer that includes elements arranged in strips may be used. Edge elements of the HIFU transducer that are aligned with the ribs may be deactivated to at least partially prevent collateral heating and thermal damage in the ribs. Alternatively, a two-dimensional (2D) phased array HIFU transducer that includes elements arranged in a 2D grid may be used. Elements of the 2D phased array HIFU transducer that are aligned with the ribs and a focal point of the 2D phased array HIFU transducer may be deactivated to at least partially prevent collateral heating and thermal damage in the ribs.

SUMMARY

In order to decrease collateral heating of ribs and tissue surrounding the ribs in a patient during high-intensity focused ultrasound (HIFU) therapy, shielding material may be positioned on or adjacent to an external surface of the patient and aligned with ribs to be protected using a magnetic resonance imaging (MRI) system. The MRI system may be used to image the shielding material and the ribs to be protected, and an error of alignment between the ribs to be protected and the shielding material may be determined based on the images. The shielding or masking material may be repositioned based on the determined error of alignment, images of the shielding material and the ribs to be protected may be reacquired, and the error of alignment may be redetermined based on the reacquired images until the shielding material is aligned with the ribs to be protected.

In a first aspect, a method for shielding a volume of a patient from ultrasonic energy of an ultrasound beam includes positioning a shielding material in a first position relative to the patient. The method also includes imaging at least part of the shielding material and the volume of the patient, and determining an error of alignment between the shielding material and the volume of the patient based on the imaging. The method includes positioning the shielding material in a second position relative to the patient based on the determined error of alignment and verifying that the volume of the patient is shielded from the ultrasonic energy.

In a second aspect, a system for positioning a mask to shield a plurality of ribs of a patient from ultrasonic energy of an ultrasound beam includes an ultrasound transducer operable to emit the ultrasound beam. The system also includes an imaging system operable to image at least part of the mask and at least part of the plurality of ribs, and a mask configured to substantially block the ultrasound energy from reaching the plurality of ribs. The mask is positioned externally to a patient. The system includes a processor operatively connected to the ultrasound transducer and the imaging system. The processor is configured to receive data from the imaging system. The data represents the mask and the plurality of ribs. Images based on the received data include images in planes crossing centers, median lines, and/or longitudinal axes of the plurality of ribs and a focal point of the ultrasound transducer, and an image in a plane through the mask and perpendicular to a path of the ultrasound beam. The system also includes a display configured to display representations of a desired position of the mask and an actual position of the mask based on the images.

In a third aspect, a non-transitory computer-readable medium that stores instructions executable by one or more processors to guide the positioning of a mask to shield a volume of a patient from ultrasonic energy of an ultrasound beam includes instructions for receiving first data from an imaging system. The first data represents a first plane in the volume. The first plane is perpendicular to a beam path of the ultrasound beam. The non-transitory computer-readable medium includes instructions for receiving second data from the imaging system. The second data represents a second plane of the volume. The second plane is perpendicular to the first plane and a longitudinal axis of the volume. The second plane also passes through a focal point of an ultrasound transducer operable to emit the ultrasound beam. The non-transitory computer-readable medium includes instructions for receiving third data from the imaging system. The third data represents a third plane of the volume. The third plane is perpendicular to the second plane and crosses through the focal point of the ultrasound transducer and the longitudinal axis of the volume. The non-transitory computer-readable medium includes instructions for receiving fourth data from the imaging system. The fourth data represents at least part of the mask in a fourth plane. The fourth plane is perpendicular to the beam path. The non-transitory computer-readable medium also includes instructions for determining an intersection corresponding to the third plane in the fourth plane and instructions for displaying the intersection corresponding to the third plane superimposed on an image corresponding to the received fourth data.

In a fourth aspect, a non-transitory computer-readable medium that stores instructions executable by one or more processors to guide the positioning of a mask to shield a volume of a patient from ultrasonic energy of an ultrasound beam includes instructions for determining a location of first anatomy in the volume and a treatment region in the volume and positioning an acoustic shield relative to a high intensity focused ultrasound transducer and the first anatomy. The non-transitory computer-readable medium also includes instructions for transmitting a beam of acoustic energy with the high intensity focused ultrasound transducer to the treatment region in the volume and shielding the first anatomy of the patient within the beam from the acoustic energy with the acoustic shield.

DETAILED DESCRIPTION OF THE DRAWINGS

The present embodiments may be used to prevent or reduce acoustic energy of an ultrasound transducer from reaching ribs (or any other at-risk structures) of a patient while minimizing the loss of focus intensity. A physical mask may be inserted, pre-focally and external to the patient, in a pathway of a beam to create an external obstacle to the ultrasound. The mask blocks the acoustic energy of the beam that may otherwise be directed into the ribs in absence of the physical mask. Masking material (e.g., shielding material) of the mask may be absorbent or reflective and may be magnetic resonance (MR)-compatible. The shape of the mask may be patient-specific. The mask may be a single piece, or several independent fragments of shielding material may be used for the mask.

The present embodiments include a method to position the masking material for rib protection or for acoustic shielding of any structure. The positioning is based on magnetic resonance imaging (MRI)-guidance. Just before high intensity focused ultrasound (HIFU) treatment, the shielding material is placed and aligned with the ribs or other structure. The shielding material may be placed as close as possible to the ribs (e.g., as close as possible to skin of the patient).

The ribs and the shielding material are scanned with three dimensional (3D) MRI. When correctly aligned, each rib is coplanar with a corresponding protector of the shielding material. The coplanar alignment is based upon a conical projection along the beam path, from the ultrasound transducer, and/or from a natural focus of the ultrasound transducer. The alignment may be achieved using two or three iterations, for example, of MR control and re-positioning of the shielding material.

Figure 1:
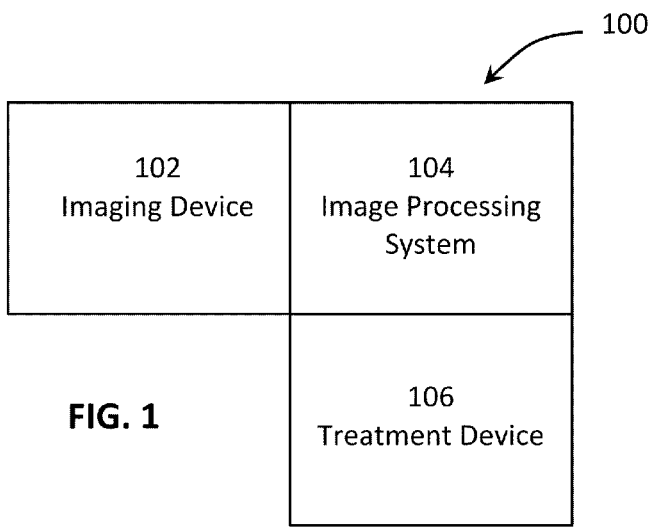
FIG. 1 shows one embodiment of an image-guided therapy system.

FIG. 1 shows one embodiment of an image-guided therapy system 100 (e.g., a therapy system). The image-guided therapy system 100 may be used in the system and method described below. The therapy system 100 may include one or more imaging devices 102 (e.g., an imaging device), one or more image processing systems 104 (e.g., an image processing system), and one or more treatment devices 106 (e.g., a treatment device). A dataset representing a two-dimensional (2D) or a three-dimensional (3D) (e.g., volumetric) region may be acquired using the imaging device 102 and the image processing system 104 (e.g., an imaging system). The 2D dataset or the 3D dataset may be obtained contemporaneously with the planning and/or execution of a medical treatment procedure or at an earlier time. Additional, different or fewer components may be provided.

In one embodiment, the imaging system 102, 104 is, for example, an MRI system. The imaging system 102, 104 may be used to create a patient model that may be used in the planning of the medical treatment procedure (e.g., HIFU therapy). For example, the image processing system 104 is a workstation for treatment planning for HIFU therapy in the liver of a patient. In other embodiments, the imaging system 102, 104 may include, for example, a medical workstation, a computed tomography (CT) system, an ultrasound system, a positron emission tomography (PET) system, an angiography system, a fluoroscopy, an x-ray system, any other now known or later developed imaging system, or a combination thereof. The workstation 104 receives data representing or images of the patient (e.g., including at least part of the liver and parts of at least some of the ribs of the patient) generated by the imaging device 102.

The treatment device 106 may be image guided by the imaging system 102, 104. The treatment device 106 may be any number of treatment devices including, for example, an HIFU transducer. The HIFU transducer 106 may use HIFU to transmit acoustic energy into tissue (e.g., of the liver). The acoustic energy heats and/or destroys the tissue through ablation. The HIFU transducer 106 may be image guided to allow treatment planning and targeting before applying the acoustic energy. In one embodiment, the HIFU transducer 106 is MRI-guided (e.g., MRgHIFU). The position, transmission, or other operation of the HIFU transducer 106 may be controlled by the image processing system 104 or another controller (e.g., a beamformer system). The therapy system 100 may include more or fewer components.

Figure 2:
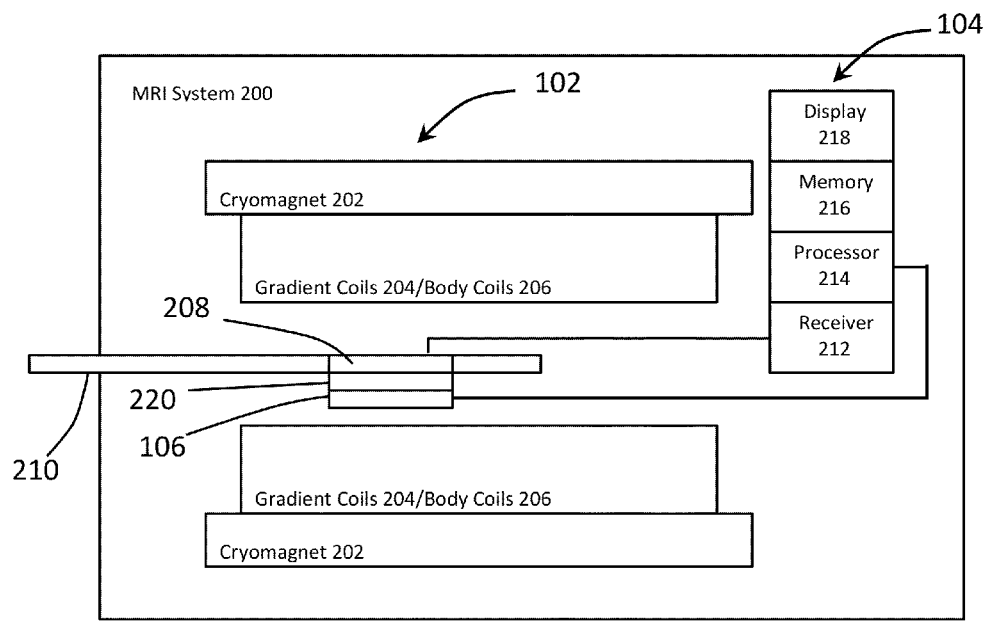
FIG. 2 shows one embodiment of a magnetic resonance imaging system.

FIG. 2 shows one embodiment of an MRI system 200. The MRI system 200 includes an MRI device 102 and the image processing system 104. The MRI device 102 includes a cryo-magnet 202, gradient coils 204, a whole body coil 206 (e.g., body coils), a local coil 208, and a patient bed 210. The image processing system 104 may include an MR receiver 212, a processor 214, a memory 216, and a display 218. Additional, different, or fewer components may be provided. For example, an additional local coil or an additional surface coil may be provided for MR imaging. Additionally, a user input device (e.g., a keyboard and/or a mouse) may be provided for user control. As another example, the local coil 208 or the whole body coil 206 is not provided.

Other parts of the MRI system 200 are provided within a same housing, within a same room (e.g., within a radio frequency cabin), within a same facility, or connected remotely. The other parts of the MRI system 200 may include cooling systems, pulse generation systems, additional image processing systems, and user interface systems. Any now known or later developed MR imaging system may be used. The location of the different components of the MRI system 200 is within and/or outside the RF cabin, such as the imaging processing, tomography, power generation, and user interface components being outside the RF cabin. Power cables, cooling lines, and communication cables connect the pulse generation, magnet control, and detection systems within the RF cabin with the components outside the RF cabin through a filter plate.

In one embodiment, the processor 214 and the memory 216 are part of the MR receiver 212. Alternatively, the processor 214 and the memory 216 are part of an archival and/or image processing system, such as associated with a medical records database workstation or server. In yet other embodiments, the processor 214 and the memory 216 are a personal computer such as a desktop or a laptop, a workstation, a server, a network, or combinations thereof. The processor 214 and the memory 216 may be provided without other components for implementing the method.

The cryomagnet 202, the gradient coils 204, and the body coils 206 are in the RF cabin, such as a room isolated by a Faraday cage. A tubular or laterally open examination subject bore encloses a field of view. A more open arrangement may be provided. The patient bed 210 (e.g., a patient gurney or table) supports an examination subject such as, for example, a patient with a local coil arrangement, including the local coil 208 (e.g., a local coil). The patient bed 210 may be moved into the examination subject bore in order to generate images of the patient. In the embodiment shown in FIG. 2, the local coil 208 is located in the patient bed 210 (e.g., below a patient). In other embodiments, the local coil 208 may be located between the patient bed 210 and the patient, on a side of the patient, and/or above the patient, for example. Received signals may be transmitted by the local coil 208 to the MR receiver 212 via, for example, coaxial cable or radio link (e.g., via antennas) for imaging.

In order to examine the patient, different magnetic fields are temporally and spatially coordinated with one another for application to the patient. The cryomagnet 202 generates a strong static main magnetic field $B_0$ in the range of, for example, 0.2 Tesla to 3 Tesla or more. The main magnetic field $B_0$ is approximately homogenous in the field of view.

The nuclear spins of atomic nuclei of the patient are excited via magnetic radio-frequency excitation pulses that are transmitted via a radio-frequency antenna, which is shown in FIG. 2 in simplified form as a whole body coil 206 and/or possibly a local coil arrangement (e.g., the local coil 208 or local coils). Radio-frequency excitation pulses are generated, for example, by a pulse generation unit controlled by a pulse sequence control unit. After being amplified using a radio-frequency amplifier, the radio-frequency excitation pulses are routed to the body coils 206 and/or the local coils 208. Each of the body coils 206 is a single-part or includes multiple coils. The signals are at a given frequency band. For example, the MR frequency for a 3 Tesla system is about 123 MHz+/− 500 kHz. Different center frequencies and/or bandwidths may be used.

The gradient coils 204 radiate magnetic gradient fields in the course of a measurement in order to produce selective layer excitation and for spatial encoding of the measurement signal. The gradient coils 204 are controlled by a gradient control unit that, like the pulse generation unit, is connected to the pulse sequence control unit. The gradient control unit, the pulse generation unit, and/or the pulse sequence control unit are represented, at least in part, by the processor 214 or another controller.

Signals emitted as a result of the excited nuclear spins are received by the local coil 208. In some MR tomography procedures, images having a high signal-to-noise ratio (SNR) may be formed using the local coil arrangement (e.g., loops, local coils). The local coil arrangement (e.g., antenna systems) is disposed in the immediate vicinity of the examination subject on (anterior), under (posterior) or in the patient. The received signals are amplified by associated radio-frequency preamplifiers, transmitted in analog or digitized form, and processed further and digitized by the MR receiver 212. The digitized data is stored in the memory 216 as complex numeric values in a k-space matrix. An associated MR image of the examination subject may be reconstructed using a one-dimensional or a multidimensional Fourier transform (FT) from the k-space matrix populated with values. Reconstructed MR images of the examination subject may be stored in the memory 216 and/or displayed on the display 218.

The local coil 208 is conductive. For example, the local coil 208 is made of copper. The local coil 208 is used as a receive antenna. Any size coil may be used. Non-symmetric size may be provided. The local coil 208 may be a surface coil or a solenoid coil. Other local coil geometries may be provided.

The local coil 208 connects with the MR receiver 212. The connection is wired (e.g., using a coaxial cable) or wireless. The connection is for data from the local coil 208 to be transmitted to and received by the MR receiver 212. The data is K-space data. In response to an MR pulse, the local coil 208 receives signals and transmits the K-space data to the MR receiver 212. Any pulse sequence may be used such as a simple pulse sequence acquiring projections along three spatial axes. Any spatial resolution may be provided (e.g., a spatial resolution of 3 mm).

The MR receiver 212 includes the processor 214 or another processor (e.g., a digital signal processor, a field programmable gate array, or an application specific circuit for applying an inverse Fourier transform) for reconstructing the K-space data. The MR receiver 212 is configured by hardware or software to calculate X, Y, and Z projection data from the K-space data.

In the course of an MR measurement, the excited nuclei induce a voltage in the local coil 208. The induced voltage is amplified by a low-noise preamplifier (e.g., LNA, preamp) and forwarded to the MR receiver 212. Other transforms for reconstructing spatial data from the K-space data may be used.

The processor 214 is a general processor, a central processing unit, a control processor, a graphics processor, a digital signal processor, a three-dimensional rendering processor, an image processor, an application-specific integrated circuit, a field-programmable gate array, a digital circuit, an analog circuit, combinations thereof, or other now known or later developed device for image processing. The processor is a single device or multiple devices operating in serial, parallel, or separately. The processor 214 may be a main processor of a computer, such as a laptop or desktop computer, or may be a processor for handling some tasks in a larger system, such as being part of the MR receiver 212 or the imaging system 104. The processor 214 is configured by instructions, design, hardware, and/or software to perform the acts discussed herein, such as guiding the positioning of a masking material for rib protection from acoustic energy emitted by an ultrasound transducer.

The memory 216 is a computer readable storage media. The computer readable storage media may include various types of volatile and non-volatile storage media, including but not limited to random access memory, read-only memory, programmable read-only memory, electrically programmable read-only memory, electrically erasable read-only memory, flash memory, magnetic tape or disk, optical media and the like. The memory 216 may be a single device or a combination of devices. The memory 216 may be adjacent to, part of, networked with and/or remote from the processor 214.

The display 218 is a monitor, a CRT, an LCD, a plasma screen, a flat panel, a projector or other now known or later developed display device. The display 208 is operable to generate images for a two-dimensional view or a rendered three-dimensional representation. For example, a two-dimensional image representing a three-dimensional volume through rendering is displayed.

FIG. 2 also shows the treatment device 106 disposed below the patient table 210. The treatment device 106 may be disposed anywhere around the examination subject (e.g., above and/or on a side of the examination subject). In one embodiment, the treatment device 106 is located in the same room or same facility as the MRI system 200.

The treatment device 106 may include, for example, an HIFU transducer and a beamformer or transmitter system. The HIFU transducer may be a spherical cap transducer. The shape of the spherical cap transducer may mechanically focus ultrasound waves into a small focal zone at a given depth. In other embodiments, the HIFU transducer may be a multidimensional transducer array, a one-dimensional transducer array, a wobbler transducer or any other now known or later discovered HIFU transducer. A wobbler transducer array is operable to scan a plurality of planes spaced in different positions within a volume. A one-dimensional array is rotated by hand or by a mechanism within a plane along the face of the transducer array or an axis spaced away from the transducer array for scanning a plurality of planes within a volume. A multidimensional array electronically scans along scan lines positioned at different locations within a volume.

The beamformer system includes, for example, a transmit beamformer with multiple channels for electrically forming a beam from an array of elements. In other embodiments, the beamformer system includes a transmitter for forming a beam with mechanical focus from a single element. The beamformer system may also include one or more lenses (e.g., a polystyrene lens) for focusing the ultrasound waves into the small focal zone, a controller for a wobbler array, filters, position sensors, combinations thereof and/or other now known or later developed components for HIFU. The treatment device 106 (e.g., the HIFU transducer and the beamformer) may be controlled by the processor 214 and/or another processor.

Using the treatment device 106, acoustic energy is transmitted into tissue (e.g., the liver) of the examination subject. In one embodiment, the treatment device 106 may be used for tissue ablation (e.g., using the HIFU transducer) in tumor treatments (e.g., of the liver). In other embodiments, the treatment device 106 may be used for hyperthermia treatments, causing cavitation, clot breaking, or for the activation of or enhanced delivery of drugs.

For ablation of a tumor on the liver of the examination subject, for example, the ultrasound waves emitted by the spherical cap HIFU transducer are focused at a natural focus point (e.g., a focal point, a focal region) of the transducer. The spherical cap transducer may be positioned relative to the examination subject, or the examination subject may be positioned relative to the spherical cap transducer, such that the natural focus point of the transducer is located at the tumor to be ablated. Pre-ablation MR images may be used to locate the tumor and position the transducer. Tissue (e.g., ribs and tissue surrounding the ribs), air-filled cavities, or interfaces between the transducer and the focal point of the transducer are subjected to the ultrasound waves emitted by the transducer. Any tissue or anatomy within the beam, even spaced from the focal region, may be subjected to the ultrasound energy during ablation treatment of the tumor. This leads to unwanted collateral heating and thermal damage in the ribs and the tissue surrounding the ribs.

A physical mask 220 is inserted in a pathway of the acoustic beam (e.g., an ultrasound beam) emitted by the transducer. The mask 220 is between the transducer and the focal region, so is pre-focally inserted between the examination subject and the HIFU transducer. The mask 220 blocks or shields the ribs and at least some of the tissue surrounding the ribs from the ultrasound waves (e.g., acoustic energy). In one embodiment, the mask 220 may substantially block the ultrasound energy that would otherwise reach the ribs (e.g., block 80 percent-100 percent of the ultrasound energy that would otherwise reach the ribs). A distance between the physical mask 220 and an external surface of the examination subject is minimized (e.g. the mask 220 is placed on the patient). The ribs are subjected to residual exposure due to elementary wave diffraction. The wave diffraction and associated residual exposure is greater for greater spacing of the mask 220 from the patient. In one embodiment, the physical mask 220 is in physical contact with the external surface of the examination subject. In other embodiments, the physical mask may be adjacent to the external surface of the examination subject, within the subject, or may be adjacent to the local coil 208.

Figure 3:
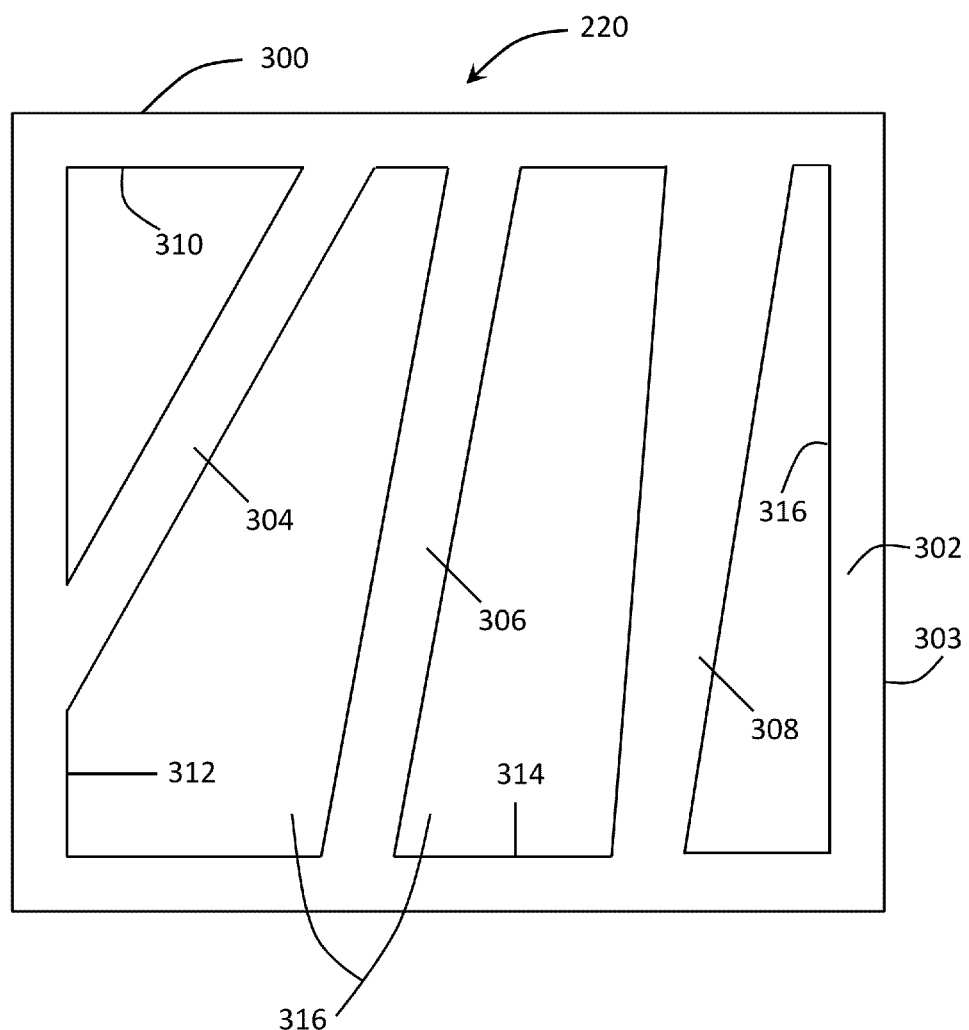
FIG. 3 shows a top view of one embodiment of a physical mask.

FIG. 3 shows a top view of one embodiment of the physical mask 220. The physical mask 220 includes an outer frame 300, a top 302, a bottom 303 (e.g., a surface of the physical mask 220 closest to the external surface of the examination subject), and a plurality of extensions 304, 306, and 308 (e.g., shields) extending between internal edges of the outer frame 300. In one embodiment, the physical mask 220 includes three shields 304, 306, and 308. The internal edges include a first internal edge 310, a second internal edge 312, a third internal 314, and a fourth internal edge 316. In one embodiment, the first shield 304 extends between the first internal edge 310 and the second internal edge 312, the second shield 306 extends between the first internal edge 310 and the third internal edge 314, and the fourth shield 308 extends between the first internal edge 310 and the third internal edge 314. The outer frame 300 and the three shields 304, 306, and 308 form a plurality of openings 318 (e.g., four openings), through which the ultrasound beam emitted by the transducer may pass. More shields may extend from and/or to different internal edges of the outer frame 300. In other embodiments, the physical mask 220 may include fewer shields (e.g., one or two shields), and/or the physical mask 220 may not include the outer frame 300. In one embodiment, the physical mask 220 includes two shields, as two ribs of the examination subject proximal to each side of a main beam axis of the ultrasound beam may be most at risk. Other ribs further from the main beam axis are less at risk given the human anatomy and a geometry of the ultrasound beam that may be used for HIFU therapy of the liver.

The physical mask 220 may be patient specific (e.g., sized and shaped to match the examination subject). The examination subject may be imaged using the MRI system 200 or another imaging system to determine sizes and shapes of the ribs to be shielded. The physical mask 220 may be made of a reflective material such as, for example, a polystyrene foam, as polystyrene foam is low cost, is readily available, is MR-compatible, is easily visualized by MRI, and may not heat up during sonication. In one embodiment, the physical mask 220 is made of an absorbent, MR-compatible material. The physical mask 220 may, for example, be made of multiple layers. Alternatively, the physical mask 220 may be a single part (e.g., include a single layer). At least one layer of the multiple layers is sufficiently rigid to provide mechanical support. At least one layer of the multiple layers, which is positioned closest to the ultrasound transducer, produces non-specular reflection of the acoustic beam. The physical mask 220 or each of the multiple layers of the physical mask 220 may be made using injection molding or extrusion, for example.

In one embodiment, cross-sections along each of the shields 304, 306, and 308, through the top 302 and the bottom 304 and perpendicular to the shields 304, 306, and 308 may be trapezoidal. For example, a thickness of the first shield 304 at the top 302 of the physical mask 220 may be greater than a thickness of the first shield 304 at the bottom 303 of the physical mask 220 at the same point along the first shield 304. The trapezoidal shape of the cross-sections may minimize magnetic susceptibility artifacts as compared to hard-edge shapes (e.g., rectangular shape). In other embodiments, other cross-sectional shapes may be used.

The physical mask 220 may be attached to the patient bed 210 in line with an aperture in the patient bed 210 using any number of fasteners including, for example, a nut/bolt combination. Alternatively, a layer of adhesive may be applied to the bottom 303 of the physical mask 220, and the layer of adhesive may attach the physical mask 220 to the external surface of the examination subject.

The physical mask 220 may be positioned relative to the examination subject such that the shields 304, 306, and 308 are positioned relative to the ribs or other anatomy to be shielded. Properly positioned, the physical mask 220 prevents or limits an amount of the acoustic energy reaching at-risk ultrasound obstacles (e.g., the ribs and the tissue surrounding the ribs), while minimizing the interruption or suppression of parts of the ultrasound beam that contribute to formation of the focal point at the tumor to be ablated. The physical mask 220 may be positioned using the MRI system 200.

Figure 4:
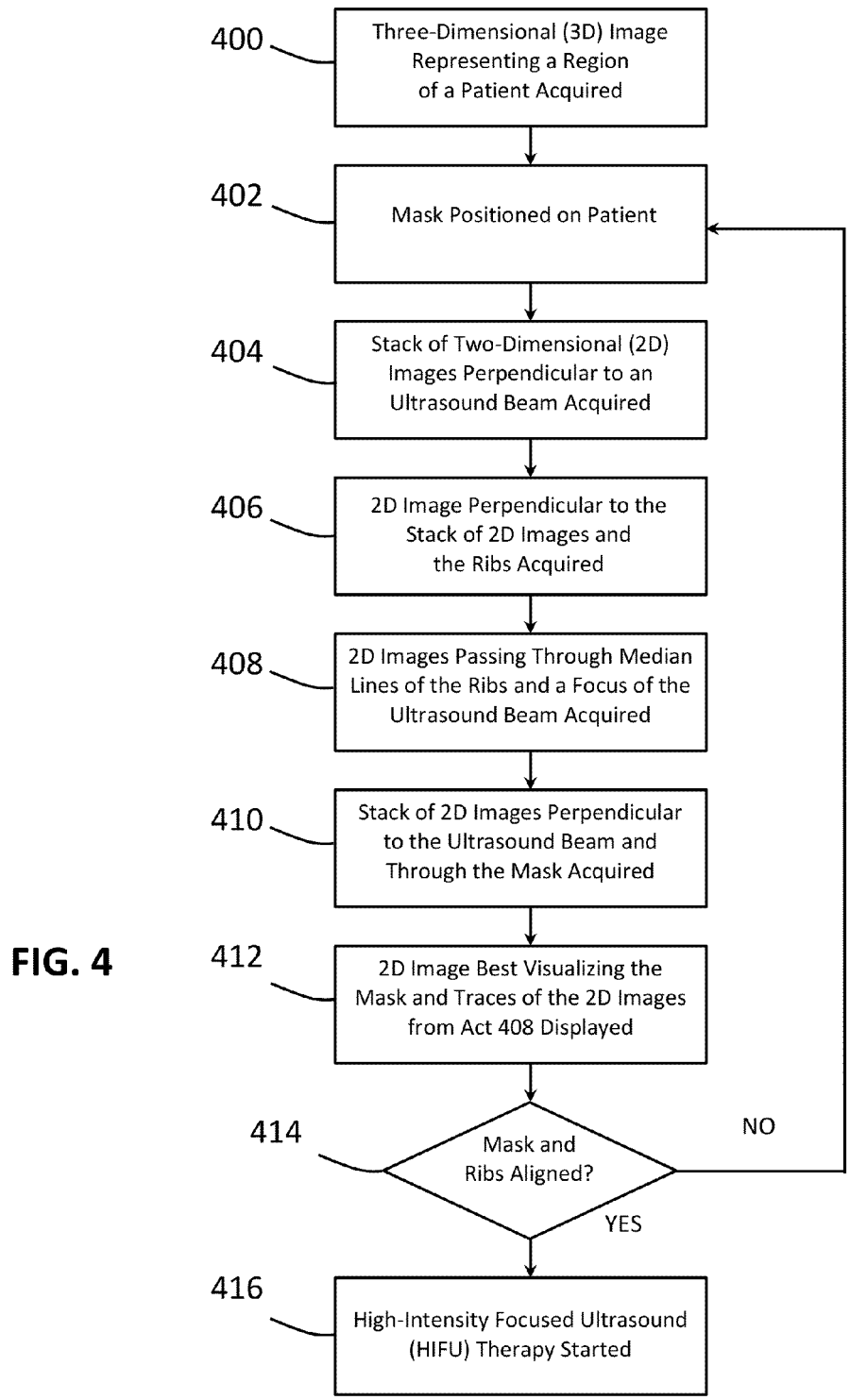
FIG. 4 shows a flowchart of one embodiment of a method for positioning a physical mask.

FIG. 4 shows a flowchart of one embodiment of a method for positioning a mask to shield a plurality of ribs of a patient from ultrasonic energy of an ultrasound beam emitted by an HIFU transducer during HIFU therapy. The method may be performed using the image-guided therapy system 100 shown in FIGS. 1 and 2 or another image-guided therapy system. The method is implemented in the order shown, but other orders may be used. Additional, different, or fewer acts may be provided. Similar methods may be used for shielding other anatomy and/or for the treatment of other anatomy than the liver.

In act 400, data representing a three-dimensional (3D) region of a patient is acquired. A 3D dataset may be acquired using an MRI device of the MRI system, and an image processing system of the MRI system may be used to process the acquired 3D dataset to construct one or more images representing the region of the patient. The region of the patient may include a tumor to be treated (e.g., ablated) and one or more regions to be protected (e.g., ribs). The 3D dataset may be acquired with a volumetric interpolated breath-hold examination (VIBE) (e.g., a 3D T1 weighted VIBE sequence) or other procedure. In one embodiment, a contrast agent may be injected intravenously to enhance the appearance of the tumor, for example.

A spherical cap HIFU transducer (e.g., a transducer) may be used in the HIFU therapy. Locations of a natural focus (e.g., a natural focal point such as the geometric center of the spherical cap of the transducer), a "South pole" and a natural focal plane (e.g., a plane containing the natural focal point and parallel to an aperture of the transducer) of the transducer may be identified in the 3D dataset and/or the image representing the region of the patient. The position of the transducer relative to the MR system and/or the patient is determined through calibration, sensors, or other process. The spatial coordinate systems of the HIFU treatment system and the MR imaging system are aligned, or a transform for relating the coordinate systems is determined. Other now known or later discovered HIFU transducers may be used in the HIFU therapy.

In act 402, a physical mask is positioned on or adjacent to an external surface of the patient, such that individual shields of the physical mask approximately align with ribs of the patient to be shielded from the ultrasound beam. The physical mask may be positioned between the transducer and the natural focal point of the transducer. The physical mask may be positioned above the patient, below the patient, and/or to a side of the patient (e.g., depending on the organ to be treated, the configuration of a patient table or bed supporting the patient, and the location of the HIFU transducer). The physical mask may be in contact with an external surface of the patient or may be positioned between a local coil of the MRI system and the transducer. The physical mask may be attached to the patient table or may be attached to the patient. A distance between the physical mask and the external surface of the patient may be minimized. The physical mask may be positioned using the 3D image representing the region of the patient as guidance. If necessary, the outer area of the patient to be masked based on projection of the tissue to be masked to the skin along a direction of the ultrasound beam may be identified from the 3D dataset.

In act 404, a stack of two-dimensional (2D) images perpendicular to a path of the ultrasound beam (e.g., images parallel to the natural focal plane and parallel to a plane of the physical mask such as coronal images or slices) is acquired. A plurality of 2D datasets representing parts of the region of the patient may be acquired using the MRI device, and the image processing system may be used to process the acquired 2D datasets to construct the stack of 2D images perpendicular to the path of the ultrasound beam. The stack of coronal images may, for example, be acquired using a T2* weighted spoiled gradient echo (FLASH 2D) sequence. The stack of coronal images may include 20 or 25 images, for example. The stack of 2D images may cover a 3D volume including the physical mask, the ribs to be protected, and the tumor. Data may be acquired every 3 mm, for example, into the patient.

Figure 5:
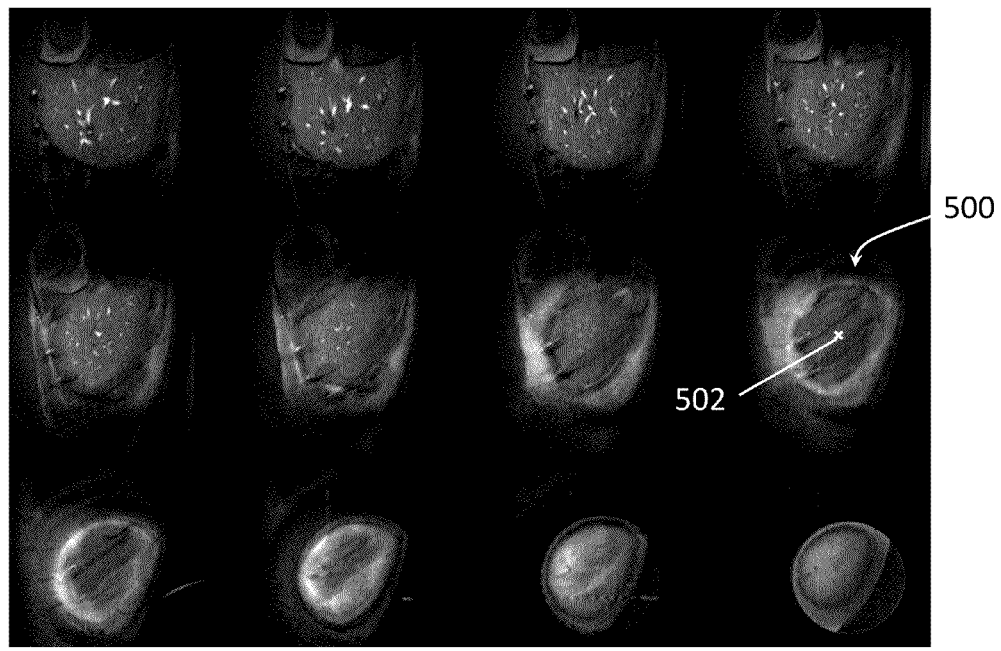
FIG. 5 shows a plurality of images from data representing planes perpendicular to an ultrasound beam.

FIG. 5 shows an example of images acquired as part of the stack of 2D images perpendicular to the ultrasound beam path in act 404. The images may be displayed on a display (e.g., a monitor, an LCD, or a touchscreen) of the image processing system. FIG. 5 shows twelve coronal images or slices. A user of the MRI system (e.g., a nurse or doctor) may identify or select an image 500 of the stack of 2D images perpendicular to the ultrasound beam that best or sufficiently visualizes the ribs. The user may select the image 500 using any number of input devices to the image processing system (e.g., a mouse, a keyboard, or by touching the display). In FIG. 5, the image 500 best visualizing the ribs is the far-right image in the second row. In alternative embodiments, the image is selected automatically, such as by identifying an image with a smoothest or largest segmented rib structure.

The image processing system determines a central acoustic axis (e.g., an axis from the transducer to the natural focus, such as a scan line; a main symmetry axis of the transducer) and determines an intersection of the central acoustic axis with the image 500 visualizing the ribs in the stack of 2D images perpendicular to the ultrasound beam path. The image processing system or another processor may determine a position (e.g., from sensors) of the transducer and thus a position of the central acoustic axis. In one embodiment, the intersection of the central acoustic axis with the image 500 visualizing the ribs may be displayed as an "X" 502, for example.

Figure 6:
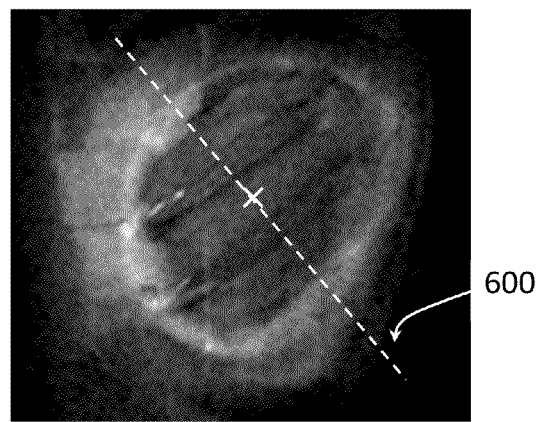
FIG. 6 shows part of a plane defining the orientation of an image to be acquired, superimposed on an image best visualizing ribs of a patient.

In act 406, a 2D image perpendicular to the stack of 2D images acquired in act 404, generally perpendicular to the ribs, and passing through the focus point of the transducer (e.g., a simple-oblique axial-to-sagittal image or slice) is acquired. A 2D dataset representing a part of the region of the patient may be acquired using the MRI device, and the image processing system may be used to process the acquired 2D dataset to construct the 2D image. The 2D image may, for example, be acquired using a T2* weighted spoiled gradient echo (FLASH 2D) sequence. FIG. 6 shows a line 600 superimposed on the image 500 visualizing the ribs from act 404. The line 600 represents the intersection of a plane defining the orientation of the 2D image in two axes with the image 500. The user may define the orientation of the 2D image in the two axes by drawing the line 600 on the image 500 using the input device. Alternatively, the image processing system may automatically define the orientation of the 2D image by orienting the plane such that the plane intersects the ribs at approximately 90 degrees relative to edges of the ribs. The 2D image acquired in act 406 shows a cross-sectional view of at least part of the ribs to be protected. The 2D image acquired in act 406 may be used to identify calculated or desired positions of the shields of the physical mask. For example, the user may draw lines on the display extending from the focal point at the tumor to centers (e.g., intersections of center lines of the ribs with the 2D image acquired in act 406) of each of the ribs. The physical mask may be aligned with the ribs when the drawn lines intersect with the shields of the physical mask.

In act 408, 2D images (e.g., two 2D images corresponding to two ribs) perpendicular to the 2D image acquired in act 406, and crossing through the focus point of the transducer and at least parts of center lines (e.g., median lines or longitudinal axes) of the ribs to be protected (e.g., through the intersections of the median lines of the ribs and the 2D image acquired in act 406) are acquired. In one embodiment, the 2D images acquired in act 408 pass through intersections of outer edges of the ribs and the 2D image acquired in act 406 instead of the intersections of the center lines of the ribs and the 2D image acquired in act 406. Two 2D datasets representing parts of the region of the patient may be acquired using the MRI device, and the image processing system may be used to process the two acquired 2D datasets to construct the two 2D images perpendicular to the 2D image acquired in act 406, and crossing through the focus point of the transducer and median lines of the ribs to be protected. The two 2D images may, for example, be acquired using a T2* weighted spoiled gradient echo (FLASH 2D) sequence.

In act 410, a stack of 2D images perpendicular to the ultrasound beam path (e.g., parallel to the physical mask) and through the physical mask (e.g., a stack of images through the physical mask) is acquired. A plurality of 2D datasets representing parts of the physical mask may be acquired using the MRI device, and the image processing system may be used to process the acquired 2D datasets to construct the stack of 2D images perpendicular to the ultrasound beam path and through the physical mask. The stack of images through the physical mask may include 3 to 5 images, for example, and the images may be centered vertically on a plane of the physical mask. The stack of images through the mask may cover a 3D volume including the entire physical mask.

Figure 7:
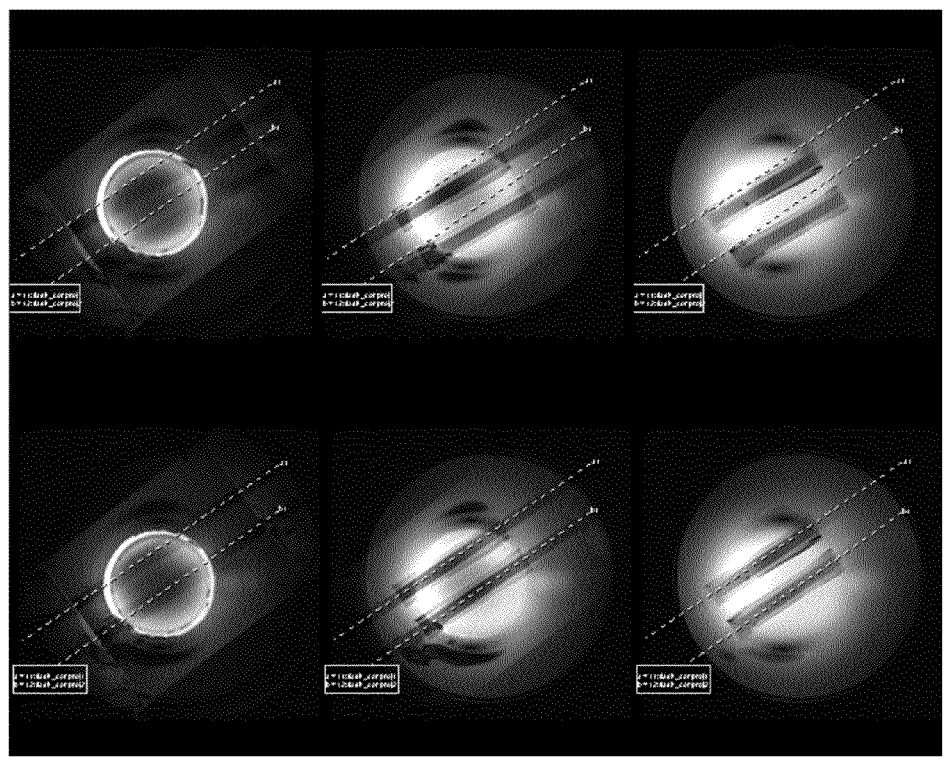
FIG. 7 shows traces representing a desired position of the physical mask superimposed on 2D images.

In act 412, a 2D image best visualizing the physical mask (e.g., acquired in act 410) is displayed, and lines or graphics of the intersection of 2D image best visualizing the physical mask with the two 2D images (e.g., two traces) acquired in act 408 are generated by the image processing system and superimposed on the 2D image best visualizing the physical mask. The lines of the intersections represent a planned, desired, or calculated position of the physical mask (e.g., target positions of central axes of shields of the physical mask), and the 2D image best visualizing the physical mask represents an actual position of the physical mask. FIG. 7 shows examples of the lines superimposed on the 2D image best visualizing the physical mask to visualize the error of alignment. As shown in FIG. 7, the traces may be represented as dotted or dashed lines. Alternatively, the traces may be represented as solid lines.

In act 414, the alignment between the physical mask and the ribs is determined. An error of alignment between the planned position and the actual position (e.g., a maximum error of alignment) may be calculated, for example, by the image processing system. The image processing system outputs a numerical value representing the error of alignment to the user, and/or the error of alignment may be measured on the display by a user. The user of the MRI system may visually determine whether the physical mask and the ribs are aligned based on the lines superimposed on the 2D image visualizing the physical mask displayed in act 412. Alternatively, the image processing system may determine whether the physical mask and the ribs are aligned based on the error of alignment calculated by the image processing system. In one embodiment, the user or the image processing system may determine whether the physical mask and the ribs are aligned within a predetermined tolerance, with the measured maximum error of alignment being less than the predetermined tolerance.

The error is a rotation, rotation direction, translation, translation direction, or combinations thereof. The mask may be rotated and/or translated in two dimensions or along the outside 3D surface of the patient. The error indicates an amount and type of offset to better align the mask with the ribs for shielding.

If the physical mask and the ribs are not aligned (e.g., the physical mask and the ribs are not aligned within the predetermined tolerance), the process moves back to act 402, and the physical mask is repositioned on the patient based on the measured or calculated error of alignment. The physical mask may be moved manually by the user of the MRI system or another user. Alternatively, the physical mask may be moved with actuators automatically or in response to an input from the user.

If the physical mask and the ribs are aligned in acts 412 and/or 414 (e.g., within the predetermined tolerance), a final verification that the physical mask is aligned with the ribs to be protected may be made. The verification may include repeating act 406. The 2D image perpendicular to the stack of 2D images acquired in act 404, generally perpendicular to the ribs, and passing through the focus point of the transducer (e.g., a simple-oblique axial-to-sagittal image or slice) may be reacquired (e.g., a reacquired 2D image). The reacquired 2D image may, for example, be acquired using a T2* weighted spoiled gradient echo (FLASH 2D) sequence.

Conic projection lines (e.g., rays originating from the natural focal point and passing through or adjacent to edges of each rib to be protected) may be generated and displayed on the reacquired 2D image. The user may draw the conic projection lines on the reacquired 2D image using an input device to the image processing system. Alternatively, the image processing system may generate the conic projection lines and display the conic projection lines on the reacquired 2D image. When the physical mask is properly aligned with the ribs, the conic projection lines intersect or reach edges of shields of the physical mask.

Figure 8:
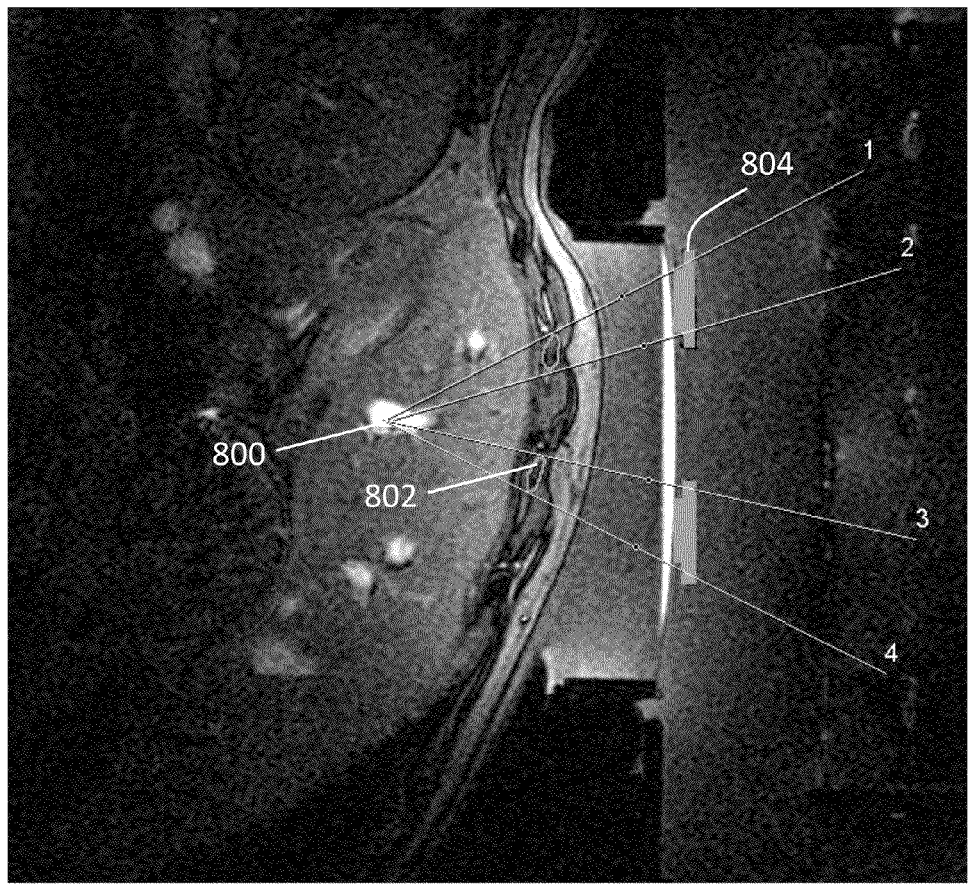
FIG. 8 shows a 2D image acquired to verify alignment of ribs to be protected and the physical mask.

FIG. 8 shows an example of the reacquired 2D image with the conical projection lines drawn on the reacquired 2D image. The conical projection lines are numbered 1-4. Each of the conical projections originates from a natural focal point 800 and passes through an edge of a rib 802 to be protected. Alignment of shields 804 of the physical mask relative to the ribs 802 is verified when the conical projections 1-4 intersect edges of shields 804 of the physical mask, as shown in FIG. 8. If one or more of the conical projections 1-4 do not intersect the shields 804 of the physical mask, the process moves back to act 402, and the physical mask is repositioned on the patient.

In act 416, the HIFU therapy is initiated with the physical mask positioned, for example, according to acts 400 to 414 discussed above. In one embodiment, the tumor on the liver of the patient is ablated using the ultrasound beam emitted by the transducer. The mask blocks part of the beam, reducing an amount of acoustic energy impinging upon the anatomy to be protected. The region to be treated is not blocked, allowing ablation, cavitation, or other treatment.

Using one embodiment of the method described above, the physical mask may be aligned with the ribs to be protected in, for example, two to four iterations. The positioning of the physical mask depends on a position of the transducer and on a position of the ribs to be protected. If electronic steering is used to move the natural focal point of the transducer and cover a 3D target volume, the physical mask may be positioned a single time before the therapy, for a full treatment session of ablation of the tumor. A loss of acoustic energy reaching the natural focal point due to the presence of the physical mask is minimal (e.g., less than 20%; depends on proximity of the physical mask to the external surface of the patient). Some residual effects due to shield edge diffraction (e.g., protector edge diffraction) may, however, be unavoidable.

While the present invention has been described above by reference to various embodiments, it should be understood that many changes and modifications can be made to the described embodiments. It is therefore intended that the foregoing description be regarded as illustrative rather than limiting, and that it be understood that all equivalents and/or combinations of embodiments are intended to be included in this description.

The invention claimed is:

1. A method for image-guided shielding a volume of a patient from high-intensity focused ultrasound (HIFU) energy of an ultrasound beam, the method comprising:
    positioning a shielding material in a first position relative to the patient, wherein the shielding material is a preformed shielding material, and the first position is outside of the patient;
    imaging at least part of the shielding material and the volume of the patient;
    determining an error of alignment between the shielding material and the volume of the patient based on the imaging;
    positioning the shielding material in a second position relative to the patient based on the determined error of alignment; and
    verifying the volume of the patient is shielded from the HIFU energy.

2. The method of claim 1, further comprising:
    re-imaging the at least part of the shielding material and the volume;
    re-determining the error of alignment; and
    re-positioning the shielding material in an updated position relative to the patient until the shielding of the volume of the patient from the ultrasound energy is verified.

3. The method of claim 1, wherein the positioning of the shielding material in the first position and the positioning of the shielding material in the second position comprise positioning the shielding material between an ultrasound transducer configured to emit the HIFU energy and a focal point of the ultrasound transducer.

4. The method of claim 1, wherein the imaging comprises imaging using a magnetic resonance imaging (MRI) device.

5. The method of claim 1, wherein the volume comprises part of a rib of the patient.

6. The method of claim 5, wherein the imaging of at least part of the shielding material and the volume comprises:
    acquiring a first image, the first image being of the volume in a first plane, the first plane being perpendicular to the ultrasound beam;
    acquiring a second image, the second image being in a second plane, the second plane being perpendicular to the first plane and the rib and crossing a focal point of an ultrasound transducer;
    acquiring a third image, the third image being of the volume in a third plane, the third plane being perpendicular to the second plane and crossing the focal point of the ultrasound transducer and at least part of a median line of the rib; and
    acquiring a fourth image, the fourth image being of the at least part of the shielding material in a fourth plane, the fourth plane being perpendicular to a beam path of the ultrasound beam.

7. The method of claim 6, further comprising:
    acquiring a plurality of first images, the plurality of first images including the first image, the first image being an image visualizing the rib; and
    acquiring a plurality of fourth images, the plurality of fourth images including the fourth image, the fourth image being an image visualizing the shielding material.

8. The method of claim 6, wherein the determining of the error of alignment comprises displaying a line of intersection of the third image superimposed on the fourth image.

9. The method of claim 8, wherein the verifying comprises:
    re-acquiring the second image; and
    displaying projection lines, the projection lines projecting from the focal point of the ultrasound transducer to edges of the rib,
    wherein the volume of the patient is shielded from the ultrasound energy when the projection lines reach edges of the shielding material.

10. The method of claim 9, further comprising treating the patient with the ultrasound beam.

11. The method of claim 1, wherein the imaging of the at least part of the shielding material and the volume of the patient comprises imaging the at least part of the shielding material with the volume of the patient.

12. The method of claim 1, wherein the positioning of the shielding material in the first position relative to the patient comprises positioning the shielding material in the first position at or adjacent to an external surface of the patient.

13. A system for positioning a mask to shield a plurality of ribs of a patient from high-intensity focused ultrasound (HIFU) energy of an ultrasound beam, the mask being a preformed mask, the system comprising:
    an ultrasound transducer operable to emit the ultrasound beam;
    an imaging system operable to image at least part of the mask and at least part of the plurality of ribs;
    the mask configured to substantially block the HIFU energy from reaching the plurality of ribs, the mask being positioned externally to the patient;
    a processor operatively connected to the ultrasound transducer and the imaging system, the processor being configured to receive data from the imaging system, the data representing the mask and the plurality of ribs, images based on the received data comprising images in planes crossing parts of longitudinal axes of the plurality of ribs and a focal point of the ultrasound transducer, and an image in a plane through the mask and perpendicular to a path of the ultrasound beam; and
    a display configured to display representations of a desired position of the mask and an actual position of the mask based on the images.

14. The system of claim 13, wherein the mask is made of acoustically reflective or absorbent polystyrene foam.

15. They system of claim 13, wherein the imaging system comprises a magnetic resonance imaging (MRI) device.

16. The system of claim 13, wherein the processor is configured to calculate an error of alignment between the desired position of the mask and the actual position of the mask.

17. The system of claim 13, wherein the processor being configured to receive the data comprises the processor being configured to:
- receive first data from the imaging system, the first data representing the plurality of ribs in a first plane, the first plane being perpendicular to the path of the ultrasound beam;
- receive second data from the imaging system, the second data representing the plurality of ribs in a second plane, the second plane being perpendicular to both the first plane and the plurality of ribs;
- receive third data from the imaging system for each rib of the plurality of ribs, the third data representing the plurality of ribs in third planes, the third planes being perpendicular to the second plane and crossing the focal point of the ultrasound transducer and parts of median lines of the plurality of ribs; and
- receive fourth data from the imaging system, the fourth data representing the at least part of the mask in a fourth plane, the fourth plane being perpendicular to the path of the ultrasound beam.

18. In a non-transitory computer-readable medium that stores instructions executable by one or more processors to guide the positioning of an acoustic shield to shield a volume of a patient from ultrasonic energy of an ultrasound beam, the acoustic shield being a preformed acoustic shield, the instructions comprising:
- determining a location of first anatomy in the volume and a treatment region in the volume, the acoustic shield being positioned relative to a high intensity focused ultrasound (HIFU) transducer and the first anatomy, outside of the patient;
- imaging at least a first portion of the acoustic shield and the volume of the patient, the acoustic shield being repositioned relative to the HIFU transducer and the first anatomy based on the imaging;
- imaging at least a second portion of the acoustic shield and the volume of the patient after the repositioning;
- verifying an alignment of the acoustic shield relative to the volume of the patient; and transmitting a beam of acoustic energy with the high intensity focused ultrasound transducer to the treatment region in the volume, the first anatomy of the patient within the beam being shielded from the acoustic energy with the acoustic shield.

19. The computer readable medium of claim 18, wherein the acoustic shield is external to the body of the patient.

20. The non-transitory computer-readable medium of claim 18, wherein the imaging of at least the first portion of the acoustic shield and the volume of the patient comprises:
- receiving first data from an imaging system, the first data representing a first plane in the volume, the first plane being perpendicular to a beam path of the ultrasound beam;
- receiving second data from the imaging system, the second data representing a second plane of the volume, the second plane being perpendicular to the first plane and a longitudinal axis of the volume, and passing through a focal point of the HIFU transducer operable to emit the ultrasound beam;
- receiving third data from the imaging system, the third data representing a third plane of the volume, the third plane being perpendicular to the second plane and crossing through the focal point of the HIFU transducer and the longitudinal axis of the volume;
- receiving fourth data from the imaging system, the fourth data representing at least part of the acoustic shield, which is positioned relative to the volume, in a fourth plane, the fourth plane being perpendicular to the beam path;
- determining an intersection corresponding to the third plane in the fourth plane; and
- displaying the intersection corresponding to the third plane superimposed on an image corresponding to the received fourth data, the acoustic shield being repositionable relative to the volume based on the displayed intersection, and
- wherein imaging at least the second portion of the acoustic shield and the volume of the patient after the repositioning comprises:
- receiving updated first data, updated second data, updated third data, and updated fourth data after the acoustic shield is repositioned relative to the volume.

21. The non-transitory computer-readable medium of claim 20, wherein the instructions further comprise calculating an error of alignment between the intersection corresponding to the third plane and at least the part of the acoustic shield in the fourth plane.

22. The non-transitory computer-readable medium of claim 21, wherein the calculating the error of alignment comprises measuring an offset between the intersection corresponding to the third plane and a longitudinal axis of the acoustic shield in the fourth plane.

23. The non-transitory computer-readable medium of claim 20, wherein the instructions further comprise iteratively receiving the first data, the second data, the third data, and the fourth data until the calculated error of alignment is less than a predetermined allowed error of alignment.

24. The non-transitory computer-readable medium of claim 20, wherein the verifying comprises:
- displaying another image, the other image being based on the second data; and
- generating projection lines from the focal point of the HIFU transducer and extending through edges of the volume in the other image,
- wherein the alignment of the acoustic shield relative to the volume is verified when the projection lines intersect edges of the acoustic shield in the other image.

* * * * *